(12) United States Patent
McKinley (10) Patent No.: US 9,095,391 B2
(45) Date of Patent: Aug. 4, 2015

(54) OSSEOINTEGRATION AND BIOINTEGRATION COATINGS FOR BONE SCREW IMPLANTS

(75) Inventor: Laurence M. McKinley, Escondido, CA (US)

(73) Assignee: AEOLIN LLC, Escondido, CA (US)

( * ) Notice: Subject to any disclaimer, the term of this patent is extended or adjusted under 35 U.S.C. 154(b) by 1554 days.

(21) Appl. No.: 12/137,043

(22) Filed: Jun. 11, 2008

(65) Prior Publication Data

US 2008/0306554 A1 Dec. 11, 2008

Related U.S. Application Data

(60) Provisional application No. 60/943,271, filed on Jun. 11, 2007.

(51) Int. Cl.
| | | |
|---|---|---|
| A61L 27/54 | (2006.01) | |
| A61B 17/58 | (2006.01) | |
| A61B 17/86 | (2006.01) | |
| A61L 31/08 | (2006.01) | |
| A61B 17/00 | (2006.01) | |
| A61F 2/00 | (2006.01) | |
| A61F 2/30 | (2006.01) | |

(52) U.S. Cl.
CPC ............ *A61B 17/866* (2013.01); *A61B 17/86* (2013.01); *A61B 17/8605* (2013.01); *A61L 31/08* (2013.01); *A61B 2017/00004* (2013.01); *A61F 2/0077* (2013.01); *A61F 2002/30067* (2013.01); *A61F 2310/0052* (2013.01); *A61F 2310/0073* (2013.01); *A61F 2310/0085* (2013.01); *A61F 2310/0097* (2013.01); *A61F 2310/00395* (2013.01); *A61F 2310/00407* (2013.01); *A61F 2310/00592* (2013.01); *A61F 2310/00598* (2013.01); *A61F 2310/00616* (2013.01); *A61F 2310/00796* (2013.01); *A61F 2310/00856* (2013.01); *A61F 2310/00928* (2013.01); *A61L 2430/02* (2013.01)

(58) Field of Classification Search
CPC ..................................................... A61B 17/866
USPC ........................................................... 606/76
See application file for complete search history.

(56) References Cited

U.S. PATENT DOCUMENTS

| | | | | |
|---|---|---|---|---|
| 4,615,705 A | * | 10/1986 | Scales et al. | 424/422 |
| 4,854,311 A | * | 8/1989 | Steffee | 606/66 |
| 4,950,270 A | * | 8/1990 | Bowman et al. | 606/916 |

(Continued)

OTHER PUBLICATIONS

"Antimicrobial effects and human gingival biocompatibility of hydroxyapatite sol-gel coatings." J Biomed Mater Res B Appl Biomater. Jan. 2006;76(1):169-78.*

(Continued)

*Primary Examiner* — Christian Sevilla
(74) *Attorney, Agent, or Firm* — KPPB LLP (57) ABSTRACT

Novel orthopaedic bone screws/spinal pedicle screws and implants that include coatings to help promote a structurally stable interface between the implant and the patient's bone/tissue, and methods of coating such screws and implants are provided. The implants and methodologies described involve at least a coating that facilitates osseous integration, and additionally at least one coating that either reduces the risk of infection in immunologically suppressed patients and/or for utilization in patients who have infection, but who require stabilization, or coatings that permit the use of dissimilar metals and prevent galvanic corrosive reactions.

19 Claims, 2 Drawing Sheets

(56) References Cited

U.S. PATENT DOCUMENTS

| | | | | |
|---|---|---|---|---|
| 4,976,736 | A * | 12/1990 | White et al. | 424/423 |
| 5,312,412 | A * | 5/1994 | Whipple | 606/96 |
| 5,348,026 | A * | 9/1994 | Davidson | 128/898 |
| 5,707,647 | A * | 1/1998 | Dunn et al. | 424/443 |
| 6,582,470 | B1 * | 6/2003 | Lee et al. | 623/23.55 |
| 6,692,498 | B1 * | 2/2004 | Niiranen et al. | 606/70 |
| 7,048,792 | B2 * | 5/2006 | Axen et al. | 106/692 |
| 7,226,612 | B2 * | 6/2007 | Sohier et al. | 424/426 |
| 2002/0045921 | A1 * | 4/2002 | Wolinsky et al. | 607/61 |
| 2004/0033241 | A1 * | 2/2004 | Donovan | 424/239.1 |
| 2004/0153125 | A1 * | 8/2004 | Roby | 606/228 |
| 2006/0142772 | A1 * | 6/2006 | Ralph et al. | 606/76 |
| 2007/0026043 | A1 * | 2/2007 | Guan et al. | 424/426 |

OTHER PUBLICATIONS

Albrektsson, "Hydroxyapatite-Coated Implants: A Case Against Their Use", J. Oral. Maxillofac. Surg., 1998, vol. 56, pp. 1312-1326.
Bach et al., "Plates Versus External Fixation in Severe Open Tibial Shaft Fractures", Clinic Orthopaedics, 1989, vol. 241, pp. 89-94.
Block et al., "Long-Term Follow-Up on Hydroxylapatite-Coated Cylindrical Dental Implants: A Comparison Between Developmental and Recent Periods", J. Oral Maxillofac. Surg. 1994, vol. 52, pp. 937-943.
Buser et al., "Soft Tissue Reactions to Non-Submerged Unloaded Titanium Implants in Beagle Dogs", J. Periodontol., 1992, vol. 63, pp. 225-235.
Cochran, "A Comparison of Endosseous Dental Implant Surfaces", J. Periodontol., 1999, vol. 70, pp. 1523-1539.
De Bruijn et al., "Bone Induction by Implants Coated with Cultured Osteogenic Bone Marrow Cells", Adv. Dental. Res., 1999, vol. 13, pp. 74-81.
De Groot, "Macropore Tissue Ingrowth: a Quantitative and Qualitative Study on Hydroxyapatite Ceramic", Biomaterials, 1986, vol. 7, pp. 137-143.
Ducheyne et al., "The Effect of Hydroxyapatite Coatings on the Metal Ion Release from Porous Titanium and Cobalt-Chromium Alloys", Trans. Orthopaedic Res. Soc., 197, vol. 13, pp. 315.
Forster et al., "Bactericidal Activity of Antimicrobial Coated Polyurethane Sleeves for External Fixation Pins", Journal of Orthopaedic Research, 2004, vol. 22, pp. 671-677.
Freeman et al., "Bone Response to a Titanium Aluminum Nitride Coating on Metallic Implants", J. Mater. Sci. Mater. Med., 2006, vol. 17, No. 5, pp. 465-470.
Hacking et al., "Acid-etched Microtexture for Enhancement of Bone Growth into Porous-Coated Implants", Bone Joint Surg. (Br)., 2003, vol. 85-B, pp. 1182-1189.

Khatod et al., "Outcomes in Open Tibia Fractures: Relationship Between Delay in Treatment and Infection", Journal of Trauma, 2003, vol. 55, pp. 949-954.
Klinger "Proteoglycans at the Bone-Implant Interface", Crit. Rev. Oral Biol. Med., 1998, vol. 9, No. 4, pp. 449-463.
Laing "Compatibility of Biomaterials", Biocompatibility of Biomaterial Orthopaedic Clinics of North America, 1973, vol. IV, C M Ebarts, pp. 249-273.
Leach et al., "Trends in Infection Prophylaxis in Orthopaedics", J. R. Coil Surg. EDINB, 1992, vol. 37, pp. 265-266.
Matter et al., "Klinische Ergebnisse mit der Limited Contact DCP— Platte aus Titan—eine prospektive Studie mit 504 Fallen", Z Unfalichir. Vers. Med., 1994, vol. 87, pp. 6-13.
Nakamoto et al., "Use of Fibrinolytic Agents to Coat Wire Implants to Decrease Infection", Investigative Radiology, 1995, vol. 30, pp. 341-344.
Olefjord et al., "Surface Analysis of Four Dental Implant Systems", Int. J. Oral Maxillofac. Implants, 1993, vol. 8, pp. 32-40.
Osborn, J. F. et al., "The Material Science of Calcium Phosphate Ceramics", Biomaterials, 1(2), 108 (1980), 1980, 108-111.
Piattelli et al., "Bone Reactions to Anorganic Bovine Bone (Bio-Oss) Used in Sinus Augmentation Procedures: A Histologic Long-Term Report of 20 Cases in Humans", Int. J. Maxillofac. Implants, 1999, vol. 14, pp. 835-840.
Portoles et al., "Reduced Bacterial Adhesion to Heparin-surface-modified Intraocular Lenses", J. Cataract Refract Surg., 1993, vol. 19, pp. 1993.
Sims et al., "External Fixation—The Incidence of Pin Site Infection: A Prospective Audit", Journal of Orthaepedic Nursing, 2000, vol. 4, pp. 59-63.
Soballe et al., "Gap Healing Enhanced by Hydroxyapatite Coating in Dogs", Clinical Orthopaedics, 1991, vol. 272, pp. 300-307.
Trisi et al., "Human Histologic and Histomorphometric Analyses of Hydroxyapatite-Coated Implants After 10 Years of Function: A Case Report", Int. J. Oral Maxillofac. Implants, 2005, vol. 20, No. 1, pp. 124-130.
Vaudaux et al., "Role of Host and Bacterial Factors in Modulating Staphylococcal Adhesion to Implanted Polymer Surfaces", J. Biomater. Appl., 1990, vol. 5, pp. 134-153.
Venable et al., "The Effects on Bone of the Presence of Metals based Upon Electrolysis", Ann Surg. 1937, vol. 105, pp. 917-938.
Vercaigne, "A Mechanical Evaluation of TiO2-gritblasted and Ca-P Magnetron Sputter Coated Implants Placed into the Trabecular Bone of the Goat: Part 1", Clinical Oral Implants Research, 2000, vol. 11, No, 4, pp. 305-324.
Yang et al., "Enhancing Osseointegration Using Surface-Modified Titanium Implants", JOM, Surface Modification in Bioapplications, 2007, pp. 71-76.

* cited by examiner

OSSEOINTEGRATION AND BIOINTEGRATION COATINGS FOR BONE SCREW IMPLANTS

RELATED APPLICATIONS

The current application claims priority to U.S. Provisional Application No. 60/943,271, filed Jun. 11, 2007, the disclosure of which is incorporated herein by reference.

FIELD OF THE INVENTION

The current invention is directed towards coatings for improving implant fixation, reducing infection and rejection rate and preventing electrolytically induced corrosion in orthopaedic implants; and more particularly to screws for implantation into bone incorporating said coatings.

BACKGROUND OF THE INVENTION

The successful integration of an implant in a patient is dependent on many factors including the extent of integration of the implant into the body, the prevention of infection, and proper material compatibility.

Historically, an orthopaedic fixation was applied to stabilize fractures and maintain the reduction of a deformity. For example, the earliest fixation methods involved the use of loops of silver wire, which were passed around the spinous process to immobilize the spine in cases of tuberculosis. Later, attempts were made to wire supporting rods made of synthetic material and/or iron to the spine to maintain stabilization. But, because these were ferrous materials, electrolytic reactions occurred, infections developed, and the results were generally unsatisfactory.

Over the years there has been an evolution to the use of different materials for stabilization, internal splintage and fixation. For example, by the 1930s Venable and Stuck, two orthopedists in Texas, identified that the use of an orthodontic alloy called Vitallium was very suitable in orthopaedics. (See, Venable C. S., et al., Ann Surg. 105, 917-938 (1937), the disclosure of which is incorporated herein by reference.) The material was unreactive with the tissues and indeed this stainless steel alloy was the main material for internal fixation and stabilization for the next sixty years. However, because of changing imaging technologies, stainless steel alloys, which produced greater artifacts during the imaging process, have been replaced by other materials, such as titanium. In addition, stainless steel alloys always had the complication that they were surrounded by a fibrous scar, which encapsulated the device. Titanium, on the other hand, functions more like a ceramic material, in that bone actually grows into the interstices of the crystalline lattice structure of the material producing superior fixation.

However, some of the physical properties of titanium are not as desirable as stainless steel. For example, stainless steel alloys have a very high rigidity-titanium of equal size has only 54% of the rigidity of stainless steel. In addition, the yield strength of titanium, i.e., the load required to statically deform the internal crystalline structure of the material is 2.34 times greater in commercially pure titanium than in stainless steel alloys, which results in some contoured implants straightening out after they have been contoured to match the body. The difference between the ultimate strengths of the two materials, titanium is less rigid than stainless steel having only half the rigidity of most stainless steel alloys.

In addition to the implantation concerns, another area of concern is infection caused by the introduction of the implant into the patient or the use of an implant in a clinical setting where increased rate of infection in immuno-suppressed patients is prevalent. The treatment of infected implants is quite controversial. There are those who feel that the removal of the implant is the only way to eradicate the infection. However, there are others who feel that the removal of the implant promotes instability, condition.

For example, often it is found that the implant becomes problematic because bacteria hide in the interstices of the crystalline structure of the metal or nonmetal implant. This makes the eradication of infection difficult. On the other hand, the clinical challenge is that if the internal stabilizing system is removed, the deformity can recur and stability may be lost, which can effect neurological and vascular function and/or result in a great increase in the patient's pain and discomfort. Moreover, the incidence of chronic infection in the United States is increasing as more and more antibiotic resistant bacteria are spreading through hospitals, extended care facilities and the community.

As a result, all too often patients have delayed recovery because of infection, implants are removed, and patients are treated with the implant removed. Because of the enormous surgical and clinical complications that can arise from such drastic revision surgery, it is often the case that patients are faced with a less than perfect clinical outcome.

One final complication that can arise is an adverse interaction between one or more components of the implants. For example, it can often be the case that orthopaedic implant systems would be made more suitable by the use of a variety of metal materials in the different components. However, galvanic interaction between the metal types can lead to serious degradation of the implant. As a result, typically a single less than perfect material is used for all of the components of the implant system to ensure against such adverse interactions.

In short, for vertebral stabilization systems, such as bone/pedicle screws, the integration of the implant is dependent on the development of a healthy screw bone interface at a macroscopic and microscopic level. Also, because metal is rigid and unyielding and bone is a living cellular structure with a crystalline scaffolding, as the metal component compresses it can distort the crystalline lattice and the cellular component of bone leading to bone implant interface loosening. However, while all patients face these challenges, there are special circumstances where patients, in the course of their life, have developed decreased bone mineralization. The crystalline lattice is weaker. There is less cellular response, and therefore, fixation between bone and metal is less satisfactory.

An exemplary group of patients that fall within this at-risk category are elderly patients who have osteoporosis, osteopenia or osteomalacia. These patients are a challenge for fixation systems in orthopaedics because the structural strength of the bone has been diminished by biological or pathological processes, i.e., osteopenia, ovariectomized patients, postmenopausal patients, patients with low serum testosterone, and patients who have suffered from radiation, etc., and other cases of medically induced osteopenia.

It is these special groups of patients who most often have orthopaedic interventions that are fraught with complications, ultimately producing fixation failure. One way to avoid such outcomes would be to develop improved coating systems that could address fixation, infection, and material interaction. Unfortunately, to-date such coating systems have not been applied to bone/pedicle screws or any of the associated hardware.

SUMMARY OF THE INVENTION

The current invention is directed to novel orthopaedic bone/pedicle screws that include coatings to help promote the interface between the implant and the patient's bone/tissue.

In one embodiment, the invention is directed to a coating and method of coating spinal or orthopaedic bone/pedicle screw implants to facilitate osseous integration.

In another embodiment, the invention is directed to a coating and method of coating spinal or orthopaedic bone/pedicle screw implants to reduce the risk of infection in immunologically suppressed patients and/or for utilization in patients who have infection, but who require stabilization.

In still another embodiment, the invention is directed to a coating and method of coating spinal or orthopaedic bone/pedicle screw implants to permit the use of dissimilar metals and avoid the galvanic corrosive reactions.

In still yet another embodiment, the invention is directed to a system including a coated bone/pedicle screw implant and other associated fixation hardware.

BRIEF DESCRIPTION OF THE DRAWINGS

These and other features, aspects, and advantages of the present invention will be more fully understood when considered with respect to the following detailed description, appended claims, and accompanying drawings, wherein:

DETAILED DESCRIPTION OF THE INVENTION

The current invention is directed to novel orthopaedic bone/pedicle screws and hardware that include coatings to promote the interface between the implant and the patient's bone/tissue. More specifically, the current invention teaches novel orthopaedic bone screws and hardware for use with patients that have decreased bone mineralization, and more particularly to patients who have osteoporosis, osteopenia or osteornalacia. The promotion of this healthy interface in at-risk patients will involve the use a first coating that facilitates osseous integration and additionally at least one of two other types of coatings:

a) coatings that reduce the risk of infection in immunologically suppressed patients and/or for utilization in patients who have infection, but who require stabilization; and b) coatings that permit the use of dissimilar metals and prevent galvanic corrosive reactions.

Each of the above-listed coating types will be described in detail in the sections below. However, before describing the coatings in accordance with the current it is important to understand the type of orthopaedic devices to which the coatings are being applied.

A bone screw is a relatively ordinary medical implantation device having a head end that cooperates with an appropriate driver and a threaded end that anchors the screw into a bone. Such screws are usually made of titanium and perhaps finished with inert titanium nitride (gold colored finish). If it is used in a patient's pedicles, then it is called a pedicle screw.

The design of these screws is extremely complicated, as they must be engineered to attach to the stronger compact cancerous bone, and as the bone is stiffer and stronger than (soft) wood, but not so stiff or strong as metal, the screws are intermediate in form, with little taper. Screws that must attach to spongy bone have a much more open structure, like a wood screw. There has to be some taper at the end of the screw, to allow self-tapping, but then this part cannot grip the hole so well. A short end taper gives a higher pull-out force, but requires more force to insert it as the cutting is more abrupt. A longer screw would resist pull-out, but may not be possible in the body so the shape has to be optimized. The threads must be sharp to cut the bone—but must not be sharp enough to puncture a surgeon's glove.

'Regular' screws may be sized in steps of 2 mm in diameter, but bone screws may need 1 or 0.5 mm steps as well as a good selection of lengths, to fit all patients. Physiology may require a particular direction of insertion that is not likely to be perpendicular to the surface. A simple screw would press unevenly as it tightened, so a 'screw' may be an assembly with a freely rotating head. There are hundreds of designs for bone screws that differ in detail but all are essentially adaptations of 'regular' screws that use steel or titanium. In other words, a substantial amount of engineering must go into balancing the engineering details of these screws to ensure the best possible interface with the bone substrate.

Secure tissue prosthesis/implant attachment is necessary for the successful performance of most implant surgeries. For example, in load bearing orthopaedic replacements, such as joint replacements, implants are effective only if they are fixed firmly in the bone. In most fields, coatings have been developed that can be applied to the orthopaedic and spinal implants and other medical devices to improve the properties of the implant. For example, conventional porous metal and ceramic coatings have been used on dental and total joint implants to facilitate implant fixation and bone ingrowth for a number of years. In addition, implant surfaces are often modified by ion implantation or physical vapor deposition to exhibit superior hardness and wear resistance. However, these materials and techniques have never been adapted for use in bone/pedicle screws and related hardware to encourage implantation and reduce the risk of infection. In particular, such coatings need to be tailored for use on at least the thread portion of the screw, which makes intimate contact with the bone of the patient. And, such coatings need to be applied in a manner and combination which will not alter the operation of the thread, an application of such coatings that has previously not been considered. Moreover, such coatings have never been tailored to at-risk patients with decreased bone mineralization.

Applying these coating technologies to bone screws presents some unique challenges. The bone implant interface develops according to the host's tissue response to the implant surface. The response to the bioinert, biotolerant, or bioactive depends on a number of factors, i.e., the composition of the implant, its surface coatings, and/or the topography of the surface of the implant. (See, e.g., Osborn, J. F. et al., Biomaterials, 1(2), 108 (1980); and Hench L. L. & Ethridge E. C., Biomaterials: An interfacial approach, New York: Academic Press. (1982), the disclosures of which are incorporated herein by reference]. Roughening the topography of the implant by applying a porous coating or other surface treatments is designed to promote osteogenesis by enhancing osteoblast metabolic activity, and is also designed to promote cellular adhesions by increasing the available surface area and helping to stabilize the fibrin scaffold with the final goal of increasing bone attachment. For example, it has been shown that faster bone apposition can be achieved in dental implants with roughened surfaces, as compared to machine surfaces. There is nearly a linear relationship between push out/pullout failure load and surface roughness. It has been surprisingly discovered that application of such coatings to the threaded interface of bone screws can dramatically improve the strength of the connection between the screw and the bone. This in turn allows for the stable implantation of screws into patients with degraded bone structure.

In summary, the current invention, by treating the implant surface with a multicomponent coating, improves the overall biocompatibility and stability of the implant system. However, the surface coating must meet certain expectations. The surface coating should not change the bulk properties of the underlying material. It should resist chemical, electrical, mechanical, and thermal forces, and these properties should not change with time.

With these goals/challenges in mind a discussion of proposed coatings for use with bone screws and related hardware is presented below.

Coatings to Promote Osseointegration and Biointegration

Although coatings are known in the general field of orthopaedics, there is a major shift occurring that has rendered them less important. Specifically, stainless steel is less prevalent and titanium is more commonplace. It is a superior implant metal, as it does not interfere with imaging studies. It is also superior for osseointegration and the physical properties of titanium are being accommodated by the redesign of implants so that its loss of rigidity compared to stainless steel of 54% has been accommodated by larger diameter materials. The yield strength of crystalline titanium is 2.34 times greater.

However, despite these improvements in the implant materials themselves, as discussed above there are a number of special circumstances in surgery where patients, during the course of their lives, have developed decreased bone mineralization and osteopenia. The crystalline lattice is weaker. There is less cellular response and fixation between the traditional implants and bone has become less satisfactory. This group of patients who have osteoporosis, osteomalacia, and osteopenia are a challenge for spinal fixation systems, because the structural strength of the bone has been diminished by biologic or pathological processes.

For example, women who are postmenopausal who have decreased estrogen support of their bone are osteopenicles who have low serum testosterone are also osteopenic, and patients who have suffered radiation and other medically induced types of osteopenia would all benefit from implants that have been coated with substance to promote osseointegration and stimulate bone at the implant bone interface.

There are many studies that show that substances that are biomimetic applied to porous type implants produce accelerated bonding between bone and the implant. The current invention recognizes that utilizing this technology with spinal implant screws will improve clinical outcome for patients who have metabolic bone problems. Implant fixation, which can be accelerated, enhanced, and improved by the coating of that implant with osteoconduction and osteoinductive substances, such as, by solutions of calcium hydroxyapatite, calcium phosphate, fluorine, and other surface treatments.

Exemplary osteoconduction and osteoinductive coatings are described in detail in the sections below. It should be understood that these materials are only provided as examples and are not meant to be limiting.

Titanium Oxide Ceramic Coatings

Electrically insulating crystalline oxide layers can be produced on metals, such as aluminum, titanium, tantalum, and niobium. In electronics, aluminum, tantalum, and oxide layers formed on them are widely applied in producing condensers, particularly $Ta_2O_5$. The layer has good insulating properties and may well be a method for insulating dissimilar metals from galvanic corrosion. Because of $Ta_2O_5$'s excellent biocompatibility, tantalum is highly suitable for preparing implants as the technology of tantalum oxide ceramic coatings is known in condenser production. Although coating tantalum implants with a tantalum oxide ceramic layer does not involve any special difficulty, cost becomes an issue. Specifically, tantalum implants are twenty-five times more expensive than titanium implants. This seems to derive from the problems processing the tantalum. It is higher in density by a factor of 5 and it is higher in base price. As a result, titanium and not tantalum is the most widely used implant material. Producing an oxide ceramic layer on titanium poses new problems.

Such oxide ceramic layers are generally produced in the surface of titanium implants electrochemically from the bulk of the metal and are modified by heat treatment. For example, one technique is to produce a corrosion resistant 200 angstrom to 2,500 angstrom thick coherent crystalline oxide ceramic layer on the surface of titanium implants. The thickness of the layer depends on the cleanliness of the surface, the material and the temperature of the electrolyte, as well as the voltage source. Accordingly, surface preparation is critically important to the production of a successful oxide.

To prepare the surface a combination of mechanical and chemical techniques is typically used. Mechanical cleaning rids the implant surface of metal turnings and adhering contaminants. This can be avoided by using metal injection molding technology. The surface to be transformed into an oxide ceramic coating may contain many substances adhering to the implant that can be removed easily. Chemical cleaning attains a surface with high purity. Chemicals applied during processing and contaminants from the processing tools have to then be removed. This involves ultrasound washing with detergent, degreasing the xylene, rinsing with acetone, and etching with an acid mixture of HF and $HNO_3$, which solves the problem.

Turning to the coating itself, the oxide ceramic layer and a colored coating 2,000 angstroms thick are produced in several steps that involve anodic oxidation, washing, drying, and then heat treatment. The following exemplary procedure was developed for anodic oxidation. A DC source, a desired potential of 80 volts in the first step, 79 volts in the second step is attained under external control in steps less than 0.1 volts per minute in the increase of the potential. An anodic oxidation is performed in a 5 WT % acrid solution of disodium hydrogen phosphate with the electrolyte at room temperature. Identical implant material can be used to hold the implant and introduce the current. After anodic oxidation, the implants are washed free of electrolyte with high purity water in an ultrasound washer and dried at 120° C. for twenty minutes. Laboratory glassware can be used for washing and drying; heat treatment glass for thirty minutes at 300° C. In such a technique there are five basic steps:

Mechanical and chemical cleaning;
Anodic oxidation;
Washing and drying;
Thermal treatment; and
Repetition of steps two, three, and four.

Compared with implants covered by other coatings, there are improved properties of this type of oxide ceramic coating implants, including higher external hardness, greater adherence between the titanium and the ceramic oxide coating, and virtually perfect insulation between the tissue and the metal, which would prevent any development of metal/tissue interreaction.

Such oxide coated titanium implants have been extensively studied. For example, Moberg investigated vitallium plates and titanium plates in an animal study and these showed increased levels of cobalt, chromium, nickel, and molybdenum in the tissues from the sites of the plates. Sometimes a gray discoloration was found in the bone surrounding the screw holes, as well as the observed macroscopic destruction in the hard and soft tissue near titanium plates. These findings suggest that titanium plates should be removed routinely after bone healing unless they have been coated. However, discolored and/or destroyed tissue did not occur when titanium oxide ceramic coated plates were installed and, therefore, a second operation is not necessary. Ion exchange does not occur between the organism and the metal with the oxide ceramic coating. Unlike the spontaneous titanium oxide surface, constant oxidation simply does not occur with these coated materials. (Moberg, L. E., et al., J. Periodontol., 63, 225-23 (1992), the disclosure of which is incorporated herein by reference.

Porous Metal & Ceramic Coatings

In the 1970s, polymethylmethacrytate bone cement was the predominant mechanism of fixation. The cement penetrated the cancellous bone and locked into small surface irregularities on the implant. Shrinkage of the cement during curing also locked the cement onto the stem of the devices. However, problems occurred with loosening of conventional cemented total joint replacement and the search began for better fixation systems. These problems were solved by the introduction of porous metal coatings. Porous metal coated implants provided enhanced fixation to either cement interlocks or the porous structure was fixated by ingrowth of bony tissue. The bone implant interface develops according to the host tissue response to the implant surface, which can be bioinert, biotolerant, or bioactive, depending on its chemical composition and topography. Roughening the topography of the implant by applying a porous coating may promote osteogenesis by enhancing osteoblast metabolic activity, cellular adhesion, increasing available surface area, and helping to stabilize the fibrinous scaffold with the ultimate goal of increasing bone attachment.

The porous coatings can take various forms and can be formed using a variety of techniques. For example, porous coatings can be produced by spherical metal powders made by gas atomization, also known as sintered metal. Alternatively, wires or fibers can be formed into porous pads. Using such titanium wire and fiber coatings can be attached on Ti-6AL-4V by a low temperature sintering bonding process. Alternative treatments include plasma spraying of a metal of commercially pure CP titanium on the surface of the implant, Ti-6AL-4V. Such plasma sprayed coatings are generally 500 to 1,000 μm thick. To improve bone in-growth into the porous coating, certain minimum pore sizes have to be achieved. In total joints, the minimum pore size is between 100 and 150 μm, while the pore size in cancerous bone is 400 to 500 μm.

A major concern with the use of porous coated implants in highly loaded applications is whether or not there are adequate mechanical properties in the implants, particularly fatigue strength. However, most studies have shown a reduction in fatigue strength following porous coating treatments.

Hydroxyapatite Porous Coatings

Coating calcium hydroxyapatite [$Ca_{10}(PO_4)_6(OH)_2$] on a bioinert metallic implant surface is an effective method of using bioactive calcium phosphate compounds in the human body. Biological advantages of hydroxyapatite coatings are enhancement of bone formation, accelerated bonding between the implant surface and the surrounding tissues, and the reduction of potentially harmful metallic ion release.

Hydroxyapatite has been used to coat many types of implants, including dental implant where it establishes strong interfascial bonds with titanium implants. This has been attributed to chemical bonding between the hydroxyapatite and the titanium substrate. Hydroxyapatite coatings have been applied by a plasma spray process, which is economical and efficient. The hydroxyapatite coating can also be applied to porous and nonporous titanium. In some studies, it has been demonstrated that osteoinductive material on dental implants results in bone osseous integration with the implant in one week instead of the usual three weeks when the implants were suitably treated with calcium hydroxyapatite.

Despite the proven advantages of using coatings in implants, there is some controversy about these coatings. For example, some researchers have expressed concerns about the potential for resorption and detachment of the coating leading to supposed susceptibility to infection. There are a few histological studies of long-term implantation in oral environments; however, there are no studies showing the use of such materials in implants placed fully into the body. (See e.g., Trisi et al., Int. J. Oral Maxillofac. Implants, 20(1), 124-30 (2005); C. Karabuda, et al., Int. J. Maxillofac. Implants, 14, 835-40 (1999); and Soballe K, et al., Clinical Orthopaedics, 1272, 300-307 (1991), the disclosures of which are incorporated herein by reference.)

Some of the previous concerns about the titanium hydroxyapatite interface were based on the concept that the hydroxyapatite would be "dissolved". However, recent studies showed that over time the naturally occurring oxide actually increased, preventing ion leakage and corrosion products being released into the organism. (Albrektsson, J. Oral. Maxillofac. Surg., 56, 1312-26 (1998); Ducheyne, P., et al., Trans. Orthopaedic Res. Soc., 13, 315 (1987), the disclosures of which are incorporated herein by reference.) In short, this concept that over time, with the thinning of the hydroxyapatite, more ion release would occur is not founded by the studies actually done to date.

Figure 1:
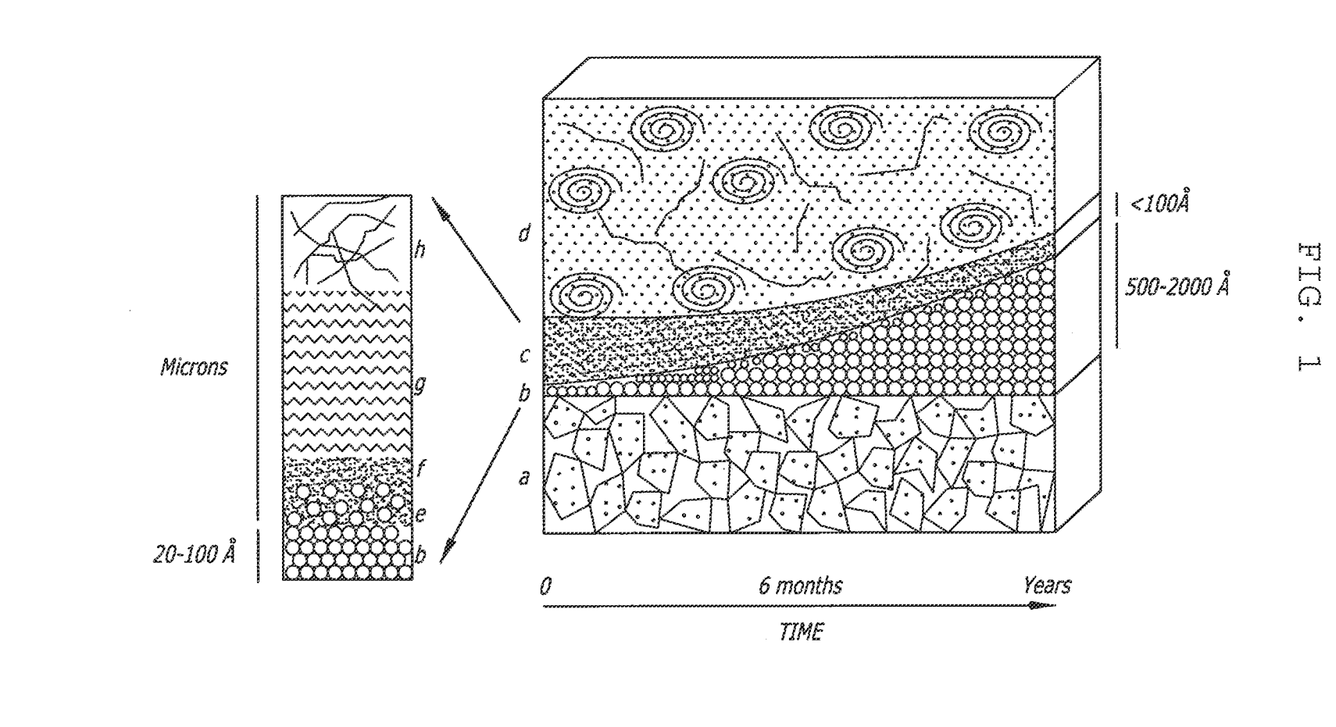
FIG. 1 is a schematic diagram of the transformation of a typical bone-implant interface over time.
Figure 2:
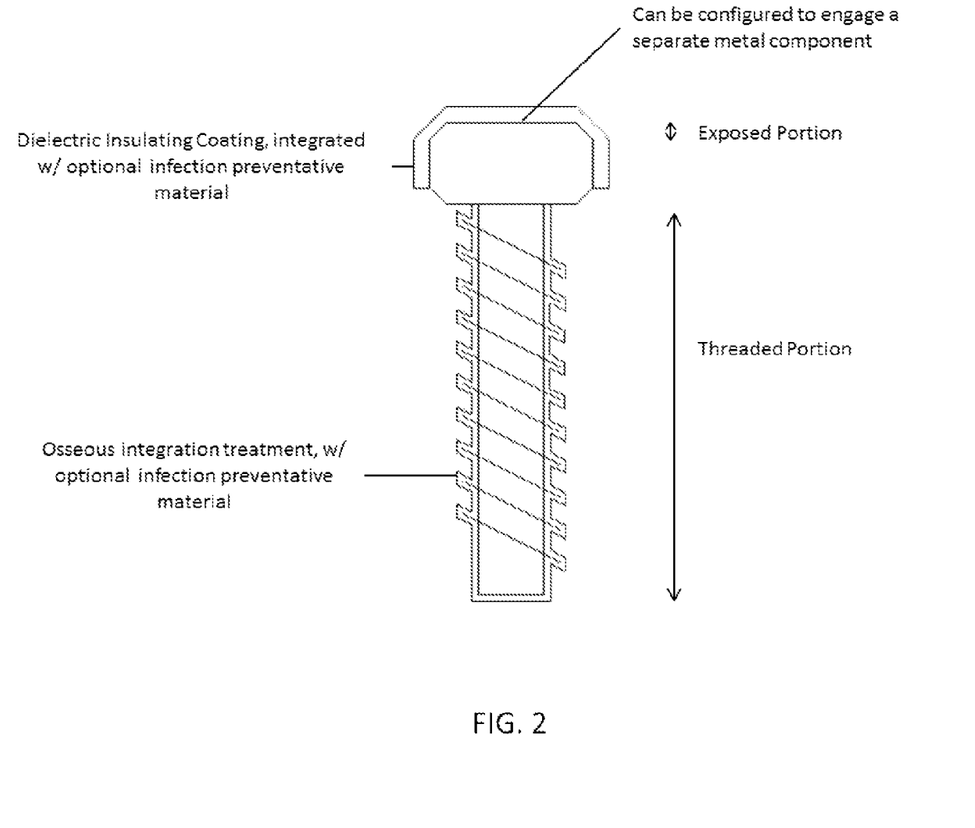
FIG. 2 depicts an implant screw with a threaded portion, an exposed portion, an osseous integration treatment, and a dielectric insulating coating, with optional infection preventing materials integrated therein.

Although not to be bound by theory, it is believed that, as shown in FIG. 1, initially, the bone (d) is several microns from the surface oxide (b), which itself is 20-100 μm thick. The gap (c) between the oxide and bone very quickly develops several layers. First, the oxide hydrates (e), followed by a layer of water (f) then a layer consisting of lipoproteins, proteoglycans, and glycosaminoglycans (g), and finally a Layer of collagen fibrils (h). The gap gradually decreases in thickness, becoming <100 μm thick over the period of 1 year or more. Conversely evidence indicates that the oxide layer increases in thickness over the same period. Although distinct boundaries exist between layers in FIG. 1 for illustrative purposes, it should be understood that there are probably few distinct boundaries in the actual interphase. (See, e.g., Albrektsson and Ducheyne, et al., cited above; Olefjord E. R. et al., Int. J. Oral. Maxillofac. Implants, 8, 32-40 (1993); and Worthington et al., J. Oral Maxillofac. Surg. 52, 937-43 (1994), the disclosures of which are incorporated herein by reference.)

Although the previous studies were focused on the use of hydroxyapatite for use in dental implants, the current invention adopts it for use in spinal fixation implants such as bone screws and hardware. To ensure proper match between the bone and implant it is preferred that hydroxyapatite with a calcium to phosphorous ratio of approximately 1.67 be coated in a layer from 100 angstroms to 2,500 angstroms thick.

Although any of the techniques previously discussed may be used to apply a calcium hydroxyapatite coating, in one embodiment, the oxide ceramic layer produced on the surface of titanium is grown electrochemically from the bulk of the metal and is modified by heat treatment. Forming the oxide ceramic layer is the final step in producing the implant with mechanical cleaning of the implant surface of metallic turnings and adhering contaminants.

Finally, although calcium hydroxyapatite has the great advantage of accelerating osseointegration on the implant, it has the disadvantage that after it stops formation the barrier-layer no longer remains between metallic titanium and the bone to prevent titanium or other contaminating ions from entering the organism. In another preferred embodiment, a fluorinated compound may be used, such as, fluorapatite to lower the solubility of the coating.

As previously discussed, the current invention combines these osseointegration coatings, such as calcium hydroxyapatite, with infection preventing antiseptics or antibiotics, improving the therapeutic effects of this technology even further.

Coating of Orthopaedic Implants to Reduce the Risk of Infection

As previously discussed, the current invention proposes the use of coatings for orthopaedic and spinal implants to improve osseointegration. For example, porous metal and ceramic coatings, such as calcium hydroxyapatite [$Ca_{10}(PO_4)_6OH_2$] may be deposited on implants to facilitate fixation and bone in-growth. However, the current invention also proposes the modification of such coatings to decrease the effects of infection.

For example, antimicrobial coatings can be used to combat the possibility of infection, which can arise from contaminated disinfectants, the hands of medical personnel who implant these devices, and autoinfection from the patient's own microflora. These infections are not easily treated. Proliferating bacteria on the surface of the implant can secrete a biofilm or slime, which is difficult, if not impossible, for antibiotics to penetrate. Moreover, the presence of bacteria can change the pH around the implant. This can result in the release of ions and the production of corrosion products. (See, e.g., P G Laing, "Biocompatibility of Biomaterial Orthopaedic Clinics of North America, Volume IV, C M Ebarts, 1973, the disclosure of which is incorporated herein by reference.)

Implant associated infections in the National Health System in Britain cost greater than £11 million per year. There is a rise in the cost because of antibiotic resistant bacteria making it even more difficult to treat infection. Infections are associated with open fractures, external fixation devices, and primary elective surgery. The frequency of infection varies between 3% and 40%. (See, e.g., Khatod M, et al., Journal of Trauma, 55, 949-954 (2003); and Sims, et al., Journal of Orthopaedic Nursing, 4, 59-63 (2000), the disclosures of which are incorporated herein by reference.) These infections result in prolonged hospitalization and the need for systemic antibiotic therapy, which has its own complications, such as deafness associated with Vancomycin, multiple IV starts, nephrotoxicity, etc. In short, the outcomes can sometimes be devastating, including amputation and death.

Moreover, the treatment of infected implants is quite controversial. There are those who feel that the removal of the implant is the only way to eradicate the infection and there are others who feel that removal of the implant promotes instability, loss of correction, or stabilization, increasing the risk of vascular or neurological problems. Such debates are made more difficult because the outcomes for patients that undergo removal are also fraught with difficulties.

It is well-known that when local antibiotics are used to supplement systemic therapy, they are effective in reducing infections. (See, e.g., Leach W S, et al., J R Coil Surg. EDINB, 37, 265-266 (1992), the disclosure of which is incorporated herein by reference.) The application of local antibiotics is seen as a positive step, but it would be even better if there was a coating that permitted sustained release of antibiotics into the environment where the infection was occurring, particularly as such a coating would decrease the amount of bacteria surrounding the coated surface. Accordingly, the current invention proposes the permeation of the osseointegration coatings with substances, such as antiseptics, antibiotics, etc. to decrease the risk of infection in patients who are immunocompromised.

A number of possible antiseptics, antibiotics, etc. are proposed for use with the current invention. For example, the use of gentamicin-coated polyurethane ("PU") sleeves have been used over external fixation pins inhibited bacterial colonization (Forster et al., Journal of Orthopaedic Research, 22, 671-677 (2004), the disclosure of which is incorporated herein by reference.) However, kinetic experiments have shown that with these materials there is an initial burst release followed by slower antibiotic release over time. Another common antibacterial impregnation material is silver, such as, for example, in the form of silver chloride, silver oxide or silver nitrate, which is a popular choice for coating implants. However, studies on the use of silver suggest that one needs to formulate the coating for either short term, intermediate, or long-term effects because it requires one type of intervention to combat the initial contamination, and much different materials to combat long-term bacterial colonization.

In the current invention it is preferable to have more regulated levels of bacteriocide released over time. It is particularly important to ensure a concentration of antibiotics above the minimal inhibitory concentration for the life of the implant. To obtain bacteriocidal activity in vivo is less than predictable due to host reactions. Moreover, persistent low levels of antibiotics below the minimal inhibitory concentration surrounding an implant have the potential to cause the development of resistant bacteria.

In particular, the current invention proposes the use of a biodegradable or nondegradeable coating system that allows the release of antibiotics or antiseptics in a controlled manner over a long time-frame, particularly for patients who:

Are immunologically suppressed;
Have chronic infection; and/or
Are in a situation where the probability of infection is high, i.e., contaminated compound fractures.

Although any conventional antibiotic materials may be used with the current invention, some materials are better suited for the proposed implants. For example, in the biomineralization process, acidic molecules play an important role in the mineralization of shell and/or bone, regulating their size and shape. Recently, researchers have described a nucleation of calcium phosphate crystals on the surface of poly 2-hydroxyethyl methylmethacrylate polymers, which are chemically modified by carboxy methylation. Acidic antibiotics, such as amoxicillin, cephamandol, carbenicillin, and cephalothin are better incorporated on such CHA coatings than basic antibiotics such as gentamicin and/or vancomycin. Carbenicillin has two carboxyl groups, cephalothin has only one, and both antibiotics are better incorporated than amoxicillin and cephamandol. Gentamicin and tobramycin do not contain carboxyl acid groups and are less incorporated into the calcium phosphate coating. Base antibiotics, including amino groups, might be coprecipitated with phosphate. On the other hand, tobramycin was better incorporated than gentamicin and this was explained by the fact that tobramycin contains five amino groups and there are only three in gentamicin. Vancomycin contains one carboxyl group, but it has the lowest incorporation rate. It also has the lowest penetration rate for bone, making it less successful for bone type infections. Likewise, calcium has difficulties binding with vancomycin resulting in poor incorporation. Although not to be bound by theory, vancomycin is a much larger molecule than many of the other antibiotics and chemically steric hindrance may limit its ability to incorporate.

In summary, it would appear that antibiotics containing carboxyl groups have a better interaction with calcium resulting in better binding and higher incorporation in calcium phosphate coatings, such as calcium hydroxyapatite. For instance, cephalothin had the highest incorporation efficiency resulting in the slowest release in PBS. The release of cephalothin was slower than for basic antibiotics indicating a diffusion rate of cephalothin whose calcium phosphate coating is slower. Ideally, however, one would want a coating that would biologically release antimicrobials or antibiotic solutions over time. Accordingly, it is important that an implant would be coated in a material that would permit release of antiseptics or antibiotics over time.

Although antibiotics, antiseptic solutions released slowly over time would be seen to be optimal compared to antibiotics that release in an initial burst and then lose their potency, as previously discussed, of particular concern would be materials that release an antibiotic below the minimum inhibitory concentration. In implants that incorporate such materials one runs the risk of developing antibiotic resistance due to the technology that has been implanted in the infected/contaminated area.

Some controlled slow release antibacterial substances have been developed an incorporated into orthopaedic bone cement. For example, Palacos® and Septopal are effective against bacteria. In addition, biodegradable polymers, such as poly lactic acid (PLA), poly-L-lactide (PLLA), poly-D-L-lactide (PDLLA), polyglycolic acid (PGA), phosphate PLA, and proteolactide coglycolide (PLGA) are all carriers of antibacterial substances that permit the slow release systems to work. However, thus far these materials have not been impregnated into or combined with an osseous integration coating, and thus there is no guarantee that the cement will adequately cover the entire surface of the implant.

The coatings of the current invention propose the incorporation of such controlled slow-release antibiotic and/or antiseptic materials, such as, for example, PLLA materials to decrease the morbidity of internal fixation stabilization in patients who have decreased immune response, active infection, and who are immunocompromised. The incorporation of such materials will in turn allow a doctor to swap out current implants with suitably coated instrumentation, as well as the installation of coated implants during the at-risk patient's initial surgery. The use of such slow release materials is to be contrasted with the common practice of impregnating or coating implants with conventional materials, such as silver and/or zinc, which are also noted to be antimicrobial, but which are not effective in that they have a high initial value, but the amounts of ions in solution are quickly reduced to levels so low that they become ineffective. Therefore, it is both medically feasible and appropriate to use these slow release materials in implant coatings. Such implants will improve the standard of care for people for foreseeable future. A more detailed discussion of both silver and polymeric antibacterial materials is provided below.

Metallic Ion Coatings

Recently research has been conducted into coating titanium implants with hydroxyapatite coatings and then modifying the coating by the addition of silver or zinc ions. Hydroxyapatite coatings containing 100 parts per million of silver ions has been shown to suppress the growth of Staphylococcus mutants. The current invention proposes the use of concentrations of up to 10,000 parts per million, which would cause an increase in suppression adjacent to the implant. In these implants there was also a clear zone of inhibition adjacent to implants coated with hydroxyapatite and zinc. Accordingly, it is also proposed that coating implants with silver and/or zinc will prevent infection, decrease infection rates, and improve biocompatibility.

Specifically, it is believed that calcium hydroxyapatite coatings incorporating silver and/or zinc will efficiently resist microorganisms and improve biocompatibility if supplied in high enough doses. The silver cation is a highly active chemical, which binds strongly to electron donor groups containing sulfur, oxygen, and nitrogen. The binding of silver to bacterial DNA inhibits a number of important transport processes, such as phosphate and succinate uptake, and interacts with cellular oxidation processes, as well as the respiratory chain. The silver ions antibacterial kill rate is directly proportional to silver concentrations; the greater the silver ion concentrations, the greater the antimicrobial activity. Accordingly, the silver ion release rate may be correlated to antimicrobial activity of coated devices. Minimal inhibitory concentrations of silver to staphylococci range from 0.5 millimoles 10 millimoles per liter. In general, other organisms such as pseudomonas are more susceptible to silver ions than staphylococci, because they have a thin murein wall or gram negative bacteria approximately one-third of the thickness of the wall of a gram positive bacteria, such as a staphylococcus. Silver ions bound to the murein by absorption induce bacteria static effects. Higher silver concentrations delivered by silver-DNA-chelate complexes also work well. Increasing hydrogen ions can displace silver ions in a competitive manner from the bacterial cell wall.

In light of these and other studies, there can be no doubt that silver ions are active against the broad spectrum of bacteria with the antimicrobial activity being proportional to the free silver ion concentrations. However, in an environment containing albumin and halide ions, the antibacterial activity of silver will be decreased as a result of specific absorption processes with the albumin and the precipitation of the silver into insoluble silver chloride. Moreover, metallic silver has only slight antibacterial affects because of its chemical stability. Accordingly, silver coated devices may only be clinically effective when the concentration of free silver ions can be increased and when contact to albumin and chloride ions, as well as possible cytotoxic effects are minimized. Because of the controversial clinical efficacy, silver are suggested for use in conjunction with other long-term slow realease agents.

Fibrinolytic Agents

Fibrinolytic agents have been used to coat wire implants to decrease infection. They have been checked in animal models. Nakamoto in 1995 showed that coating stainless steel wire implants with fibrinolytic agents prevented infection after bacterial contamination. (See, Nakamoto et al., Investigative Radiology, 30, 341-344 (1995), the disclosure of which is incorporated herein by reference.) He used a stainless steel heparin coated steel urokinase-heparin coated steel. The heparin coated wire, despite heavy contamination, showed a 40% non-infection rate. The urokinase-heparin coated wire had a 50% non-infection rate. The use of heparin to coat biomaterial has also been shown to decrease bacterial adhesion in vitro. Vaudaux in 1990 proposed that fibronectin, a multifunctional glycoprotein found in connective tissue and in blood, may play an important role in the adherence of bacteria to biomaterial. (See, Vaudaux, P., et al., J. Biomater. Appl., 5, 134-153 (1990), the disclosure of which is incorporated herein by reference.) They found that the heparin and derived dextrans inhibit the adhesion of staphylococcus aureus to fibronectin coated biomaterial. Also, Portoles, et al. in 1993 showed heparin bound to the surface of modified intraocular lenses were stable for two years and had no toxicity and greatly decreased the infection rate of intraocular lens implants. (See, Portoles M. F., et al., J. Cataract Refract Surg., 19, (1993), the disclosure of which is incorporated herein by reference.) It should be understood that any of these fibrinolytic agents may be incorporated into the implants of the current invention.

Summary

As can be surmised from the above discussion, there are a number of possible antibiotic and antiseptic coatings that can be used with implants to decrease the likelihood of infection. Any of these coatings may be incorporated into the methods and devices of the current invention.

Although the above-discussion has focused on the examples of suitable antiinfection materials for use in the implants and coatings of the current invention, any suitable slow release antibiotic and antiseptic can be incorporated into the biomimetic coatings of the current invention in order to prevent the growth of bacteria on conventional implants or prostheses. Such anti-infectious agents are preferably soluble in water and thus soluble in supersaturated calcium phosphate solutions. As such deposition of such materials onto the implant may be made through a number of conventional methods. For example, during the immersion of ACP coated titanium implants, antibiotics can be coprecipitated with carbonated hydroxyapatite crystals along the surface of the implant.

Regardless of the impregnation/coating method used, in accordance with the current invention, it is proposed that these implants will improve the biomimetic effect, decrease the risk of infection, decrease the probability of infection, and decrease the probability of significant sepsis. In addition, these coatings will decrease the rate of rejection of the implant, removal of the implant, loss of fixation, loss of stabilization, and the possibility of increased neurological deficits and/or vascular deficit. For more details see, e.g., Bach A W, et al., Clinic Orthopaedics, 241, 89-94 (1989); and Matter P, et al., Z. Unfalichir. Vers. Med., 87, 6-13 (1994), the disclosures of which are incorporated herein by reference.)

Coating of Implants to Prevent Galvanic Corrosive Reactions

Finally, although the above discussion has focused on implant coatings to improve osseous integration and prevent invention, the need to ensure minimal corrosion is also a major determining factor in the selection of materials for use in the body, particularly in a multi-component fixation system where elements of the system may be formed of different metals. Specifically, in choosing materials for use with the system the materials have to be biocompatible and not cause an adverse reaction, and the materials must withstand the body's environment. For example, the metals used in cardiovascular systems must be nonthrombogenic, so they must be more electronegative than blood, such as, cobalt chromium alloys and titanium which are used in heart valves.

Historically, the earliest attempt at repairing the human body was by Petronius in 1565 who tried to repair a cleft pallet with a gold plate. In 1665, Hieronymus Fabricius described the use of gold, iron, and bronze wires as sutures. By 1775, there were arguments by French surgeons as to what was the favored internal fixation. Was it brass wires or other materials? They referred to two French surgeons by the names of Lapeyode and Sicre who had successfully used wire loops to repair bone fractures. In 1886, Hamsmann used a metal plate for internal fixation. The plates were nickel plated steel; holes were made and screws were inserted at the bone. Roentgen, in 1895, was able to observe the healing of fractures and it showed the advantages of internal fixation, stimulating the concept.

In these early days, it was difficult to determine whether an infection or inflammation produced by lack of biocompatibility was occurring. Lord Lister emphasized sepsis, but metals tested as implants in those days were platinum, gold, silver, lead, zinc, aluminum, copper, and magnesium. Observations led to the discovery of electrochemical reactions in the body in the 1930s. Steel screws or magnesium plates produced dramatic results. Implanted magnesium plates often disappeared before the fracture healed. Combinations of copper and zinc were also highly reactive, and finally Drs. Venable and Stuck identified vitallium as the best steel alloy.

Stainless steel was discovered by Berthier in 1821 when he showed that adding chromium to iron improved corrosion resistance. The metallurgy of stainless steel is complex. Chromium is the key element in corrosion resistance and is a ferrite former, carbon is an austenitic stabilizer, and nickel is added to the steel to stabilize the austenitic phase. Molybdenum was later added in amounts of 2 to 3% to strengthen the protective surface film in saline and acidic environments. It also permits increased resistance to pitting.

Cobalt alloys, first studied in 1895 by Haynes, had many applications from aircraft engines to surgical implants. Haynes Stellite Alloy No. 21 is a cobalt, chromium, and molybdenum carbon alloy. On the other hand, titanium and titanium alloys are relatively new. Titanium was discovered in 1790. It is the eighth most common element in the earth's crust. Titanium is also at least as strong as steel, is 50% lighter, and is easily fabricated.

Metal ions released from surgical implants generally results from corrosion. Even titanium, which is highly corrosion resistant, still allows ions to be released. The significance of corrosion of metal implants is important because it adversely affects biocompatibility and mechanical integrity. Surface phylum dissolution and corrosion are two mechanisms for introducing additional ions into the body. Extensive release of metal ions can result in adverse biological reactions.

The electrochemistry of the corrosion process involves the release of positive metal ions from the reaction site [anode], such that a flow of electrons is made available to the protected site [cathode]. The two electrodes can be dissimilar metals, but also it can result from different surface areas on the same piece of metal, i.e., impurities, concentration differences of gas, etc.

Standard electromotive forces for a number of different metals are demonstrated in Table 1, below. As shown, gold is the most cathodic and potassium is the most anodic. The rate that a corrosion reaction proceeds is related to the environment, such as motion or load, or other environmental factors. The rate at which the metal corrodes also depends on kinetic factors. Following surgery, the pH can increase to 7.8 or decrease to 5.5 and then return to 7.4 over a few weeks. Infection and hematoma can cause further variation of the pH. Surface films of some metal alloys may also be dominated by certain elements. For example, chromium dominates on stainless steel and titanium oxide on titanium alloys. Other metallurgical variables influence corrosion behavior. Accordingly, corrosion resistance of the metal is specific to a number of factors, including composition, changes in metallurgical heat treatment, microstructure phases present, and surface finish.

TABLE 1

Comparison of Galvanic Activity

| Metal-Metal Ion Equilibrium | Electrode Potential Versus SHE (25° C., V) |
|---|---|
| Au—Au$^{3+}$ | 1.498 |
| Pt—Pt$^{2+}$ | 1.2 |
| Pd—Pd$^{2+}$ | 0.987 |
| Ag—Ag$^+$ | 0.799 |
| Hg—Hg$^{2+}$ | 0.788 |
| Cu—Cu$^{2+}$ | 0.337 |
| H$_2$—H$^+$ | 0.000 |
| Pb—Pb$^{2+}$ | −0.126 |
| Sn—Sn$^{2+}$ | −0.136 |
| Ni—Ni$^{2+}$ | −0.250 |
| Co—Co$^{2+}$ | −0.277 |
| Cd—Cd$^{2+}$ | −0.403 |
| Fe—Fe$^{2+}$ | −0.440 |
| Cr—Cr$^{2+}$ | −0.744 |
| Zn—Zn$^{2+}$ | −0.763 |
| Ti—Ti$^{3+}$ | −1.210 |
| Ti—Ti$^{2+}$ | −1.630 |
| Al—Al$^{3+}$ | −1.662 |
| Mg—Mg$^{2+}$ | −2.363 |
| Na—Na$^+$ | −2.714 |
| K—K$^+$ | −2.925 |

To prevent such galvanic effects, the current invention proposes the use of suitable surface coatings to make the implants dielectrically inert, affording the possibility of insulating the implant against dielectric current and from a physical chemistry standpoint reducing the possibility and probability of adverse reaction and secondary corrosive currents. Particularly in the head portion of screw inserts where the insert would be likely to be placed into contact with other components made of dissimilar metals.

Parylene Coatings

As described above, if one were to design the ideal coating, one would want to consider the following issues:
  biocompatibility;
  the inertness of the coating;
  the pure temperature should be within the performance rate of the coating system;
  conformability, the coating should be able to bind to a variable surface geometry;
  the finish thickness of the coating should be adequate to provide uncompromised physical, chemical, and electrical protection;
  mechanically the coating would be durable enough not to be effected by the physical activity of installing the instrumentation;
  the coating would be resistant to flaking;
  the coating would be sterilizeable without changing or decomposing;
  the coating should be fairly inert without any gassing, etc.; and
  the coating should isolate the surface from moisture and electrical conductivity.

One exemplary coating material that meets the above criteria, and therefore is particularly preferred for use in the current invention, is Parylene. Paralyene is a thin vacuum deposited polymer. It can be deposited on objects at room temperature. It does not require the use of solvents, catalysts, plasticizers, or other additives. It is based on a raw material called diparaxylylene, which is a white crystalline powder. A vacuum and thermal process converts the powder into the polymer, which is formed on substrates at room temperature. Some of its unique properties are:
  it conforms to substrate topography;
  it produces pinhole free coverage in very thin layers;
  it resists chemical attacks from organic solvents, inorganic reagents, and acids;
  it offers dielectric strength above 5,000 volts DC at 25 μm (1 ml of film thickness);
  it can be coated in diverse substrates, such as glass, metal, paper, resin, plastics, ceramic, ferrite, silicone, and even powdered and granular substances;
  it has low thrombogenic properties and low potential for triggering an immune response; and
  the material has been shown to be highly resistant to potentially damaging effects of corrosive body fluids, electrolytes, proteins, enzymes, lipids, etc.

There are now four versions of Parylene coatings available for medical surface modification applications:
  Parylene N, which provides particularly high dielectric strength. The dielectric constant is independent of frequency. Because of its high molecular activities during deposition, Parylene N has the highest penetrating power and is able to coat deep recesses and blind holes. It also has a low dissipation factor and dielectric constant.
  Parylene C has the chlorine atom added into the Parylene Benzene ring. This gives it a combination of electrical and physical properties, including low permeability to moisture. Parylene C deposition is substantially faster than Parylene N and, therefore, its crevice penetrating ability is reduced.
  Parylene D has two chlorine atoms added to the Benzene ring. There is a higher degree of thermal stability. Crevice penetration is the least pronounced of all of the four Parylene.
  Parylene HI is a fluorine modified Parylene coating, which can be used at temperatures as high as 450° C. High temperature Parylene coatings are suitable for electrosurgical devices, which are subject to very high instantaneous temperatures.

A comparison of the properties of the two most widely used forms, Parylene N and Parylene C are provided in Table 2, below. It should be understood that any of these materials may be used with the implants according to the current invention provided a suitable coating can be formed on the implant in question.

TABLE 2

Property Comparison of Parylene Materials

| Property | Parylene N | Parylene C |
|---|---|---|
| Crevice Penetration | Best | Good |
| Molecular Activity | Highest | Good |
| Coating Uniformity | Best | Good |
| Hardness | Least | Moderate |
| Physical Toughness | Least | Moderate |
| Moisture Resistance | Moderate | Best |
| Cost-effectiveness | Moderate | Best |
| Dielectric Strength | Best | Good |
| Dielectric Constant | Low | Higher |
| Gas Permeability | Good | Best |
| Chemical Resistance | Good | Excellent |
| Elongation to Break | Lower | Best |
| Thickness Control | Good | Best |
| Masking Complexity | Greatest | Moderate |
| Thermal Stability | Moderate | Moderate |
| Coating Speed | Lowest | Moderate |
| Dielectric Strength | Good | Good |
| Dissipation Factor | Low | Higher |
| Lubricity (CFE) | Best | Good |

Although Parylene coatings are discussed above, it should be understood that any coating or surface treatment that reduces ion release may be used with the current invention, including, for example, coating of substances such as stainless steel with titanium oxide and/or the physical treatment of the outside of the titanium implant with laser or shot peening. Also, coatings to promote particular functions, such as hydroxyapatite coating, may isolate the implant from the corrosive effects of the body.

Coating Methodologies

Although the above discussion has focused on novel combinations of coating materials for use in bone/spinal screw implants and related hardware, it should be understood that the current invention is also directed to methods of forming such coatings. This section will describe exemplary methodologies for implementing the coatings described herein.

There are three general techniques to modify the surface of an implant, i.e., adding or removing material, changing material that is already present, and the surface can also be altered through laser or electron beam thermal treatment with or without adding or removing material.

Depositing material, which is also known as a positive material transport system.

Removing material, also known as the negative material transport system.

Transforming without depositing or removing, which is known as the material transport free procedure.

Each of these techniques may be used with the current invention and will be discussed further below.

Deposition of Materials

Although there are many different techniques for depositing a material on the surface of an implant, all have in common that some extra material is being added to the implant, or in other words that there is a positive material transport to the implant. For example, in one very common technique a fine powder is applied to the surface of the object to be coated. The powder is compacted by heat treatment similar to forming an enamel layer on metal or porcelain.

The sol-gel process is a colloidal chemical method in which an organometallic compound is prepared from the metal component of the metal oxide intended for the coating and organosol formed from the compound with an organic solvent, the combination of which polymerizes into a gel on the surface of the implant. Upon drying the gel condenses, followed by heat treating to remove the solvent and the organic component. The material converts to solid form and through sintering, compacts into a very fine structured coating. The most sensitive stage in the procedure is the heat treatment on which the quality compactness and the structure of the layer depend. With this method, good quality uniform compact layer of calcium phosphate can be prepared on the surface of a titanium implant. A hydroxyapatite coating can also be prepared onto implants by procedures similar to the sol-gel process. Here, coating is done by a thermal decomposition of calcium oxide dissolved in an organic solvent, such as phosphate.

Another technique is hot pressing or plasma spraying after powdering. Technologically, plasma spraying is a variant of the classical flame spraying method. The first plasma spraying procedure for performing hydroxyapatite layers and titanium implants was reported by DeGroot in 1986. (See, DeGroot, K., Biomaterials 7, 137 (1986), the disclosure of which is incorporated herein by reference.) This was applied in vitro and in vivo. It allowed the study of the behavior of titanium implants coated with calcium phosphate layer prepared by plasma spraying. Because of its rapid cooling, plasma spraying causes an uneven coating layer on the implant surface. Unfortunately, cracks and fissures can develop.

Finally, in the last twenty years, vacuum technology has been developed and has been used to produce hardware resistant coatings. Two commercially available vacuum deposition techniques used for the manufacture of implants are:

Physical vapor deposition (PVD), in which physical deposition from the gas phase and the building up of a layer is performed; and Chemical vapor deposition (CVD) which involves deposition from the gas phase using chemical means.

In nitration, the best known PVD procedure, atomic nitrogen diffused into the surface of the implant forms a nitride with the alloying components of the metal, titanium, titanium alloys, and steel. However, because carbon diffuses simultaneously with the nitrogen, carbonitrides may also form on the substrate surface. The layer formed is very hard; it is wear resistant, corrosion resistant, and resists metal fatigue.

In CVD, readily vaporized metal halides are deposited from the vapor state in a regulated reaction chamber forming solid state compounds. These materials are deposited as a thin coating on the surface of the metal. Oxide ceramic or plastic coatings may be prepared in this way. An example would be an aluminum oxide coating. In such an example, an aluminum halide vapor would be introduced into the reaction chamber where, with oxygen, it would be deposited as an aluminum oxide layer on the surface of the implant.

Although specific deposition techniques are discussed above, it should be that any technique suitable for depositing thin coatings of materials onto implant surfaces may be used with the current invention.

In terms of what materials can be deposited using the above techniques, as discussed in the sections above numerous substances can be considered, e.g., various ceramics, including glass ceramics, apatites, plastics, plasmified titanium, and titanium oxide, as well as other metals and metal oxides. Of particular interest are calcium phosphate ceramic coatings Calcium phosphate is a substitute for hard tissue because it contains inorganic constituents of bone and teeth. In principle, compounds in the large family of calcium phosphate would be applicable as an implant coating and this includes dicalcium phosphate, dihydrate, dicalcium phosphate, hydride, octacalcium phosphate, beta-tricalcium phosphate, hydroxyapatite, tetracalcium phosphate, monoxide, and others.

One material that has been used extensively in dental implants is hydroxyapatite and beta-tricalcium. Coating materials with different properties of solubility, hardness, and porosity can be prepared from both types of calcium phosphate ceramics. Hydroxyapatite with a calcium/phosphorus ratio of 1 to 67 is most similar to bone. It has an advantage in that it accelerates osseous integration of the implant, but unfortunately, it has the disadvantage that after its transformation or resorption, a barrier layer no longer remains between the metallic titanium and the bone to prevent titanium or other contaminating ions from entering the organism that the device has been implanted in.

The leaching of materials into a patient can be an important consideration, because if there is a defect in the crystalline structure, i.e., inclusions, non-resorbable calcium phosphate can develop openings and microfissures on the surface of an implant. Certain parts can dissolve, opening up channels between the metal and the tissue in the organism. In this way, it is also opening up the implant to corrosion. One solution to this leaching problem is to use materials with lower solubility. For example, the fluorine in fluoroapatite $[Ca_5(PO_4)_3F]$ results in a lower solubility which reduces the affect of fluoride on implants. In addition, crystalline oxyapatite, as well as beta-wollastonite and beta-whitlockite may be used also.

Negative Material Transport

Another way to condition the surface of an implant that may be used in the current invention in conjunction with the coating deposition techniques described above is through the removal of material, also known as negative material transport system. Here, two layers of different origins that form during processing must be removed from the implant surface. One layer comprises the mechanically and chemically bound impurities, the other is the deformed surface part. Mechanical and chemical impurities can be removed by microscopically deburring the implant, while organic contaminants may be removed by degreasing. However, degreasing implants made from titanium and titanium alloys with halogenated, chlorinated solvents, such as freon or trichloroethane is not acceptable because of the danger of subsequent corrosion.

An alternative method is to microtexture the surface using acid etching. Such a technique is used generally secondary to a coarse surface texturing, such as grit blasting or machining of the implant screw thread, but this treatment results in a 10% to 40% increase in bone contact and a significant increase in pullout and torque strength. (See, e.g., Cochran DL, J. Periodontol 70, 1523-39 (1999), reporting a two-fold increase in pullout and torque strength, the disclosure of which is incorporated herein by reference.)

In the current invention it is proposed that such etching be combined with other coating techniques to create hybrid implants. For example, some researchers have taken an acid-etched grit-blasted implant and then subsequently coated it with hydroxyapatite by plasma spraying technology. Hacking et al., showed an 80% bone apposition due to the stimulatory effect of microtexture alone, that and this treatment can triple the speed of bone incorporation. (Hacking, S. A., et al., Bone Joint Surg. (Br). 85-B, 1182-1189 (2003), the disclosure of which is incorporated herein by reference.)

Material Transformation

Another method that may be used in the current invention in conjunction with coating deposition is to modify the implant surfaces without adding or removing material. The key is that in these processes material is neither deposited nor removed, but changes never the Less.

There are a number of techniques, such as, for example, shot peening, which is a classic procedure that improves the mechanical properties of the metal surface. A current procedure used on implants is with a Laser and electron beam. Radiation beam impinges on the surface of the metal and causes rapid local heating and cooling, which results in microstructural changes while the bulk of the material remains cold. The structure formed in this way can display improved mechanical and chemical properties. Finally, there is a method called ion implantation. It achieves metal surface alloying by bombardment with accelerated particles.

Exemplary Embodiments

Additional details concerning specific coatings and their potential uses will be explored in the following Exemplary Embodiments.

Osteoinductive and Osteoconductive Coatings

As previously discussed, in trying to improve the osseointegration of an implant with a coating, one is attempting to get adhesive biomolecules in the extracellular matrix of the bone, which will improve strength and stability at the bone implant juncture. Experimental studies have repeatedly shown that it is possible to culture osteoblastic cells on implant materials and biomolecules can be absorbed onto titanium powder. (See, e.g., Klinger M. M., Crit. Rev. Oral Biol. Med., 9(4), 449 (1998); and Freeman, C. O. & Brook, I., J. Mater. Sci. Mater. Med., 17(5), 465-70 (2006), the disclosures of which are incorporated herein by reference.)

The following exemplary embodiment are all proposed as potential implant coatings for the current invention:

Hydroxyapatite coated titanium porous coatings on titanium 6 AL-4V applied with plasma sprayed method. (Yang, et al., JOM, Surface Modification in Bioapplications, 71-76 (2007), the disclosure of which is incorporated herein by reference.)

Zirconia reinforced hydroxyapatite composite coatings. (Lee and Yang, 2004)

Surface roughening can also influence bond strength of the bioactive apatite layer on orthodontic implants, such as acid etching of the macrotexture, in combination with sol-gel-formed calcium phosphate to improve osteoconductivity of porous surface titanium alloy implants.

Implants coated with cultured osteogenic bone marrow cells. (de Bruijn, D., et al., Adv. Dental. Res. 13, 74-81 (1999), the disclosure of which is incorporated herein by reference.)

Titanium oxide quick blasted calcium phosphorous magnetron sputter coated implants, which can improve the molecular integration in the implant bone junction. (Vercaigne S, Clinical Oral Implants Research, 11(4), 305-324 (2000), the disclosure of which is incorporated herein by reference.)

In short, the above examples provide the combination of surface roughness, thickness and type of the coating that can influence the sheer strength of the implant of bone interface. As such, bone/spinal screw implant fixation can be accelerated, enhanced, and improved by the coating of implants with these and other osteoconductive osteoinductive substances by solutions of hydroxyapatite, calcium phosphate, and surface treatment in accordance with the current invention. These techniques need to be particularly seen as a mechanism to enhance fixation of implants in patients whose underlying bone structure, bone density, and bone quality has been impaired by disease and age.

Immunological Coatings

As previously discussed, the current invention also contemplates the integration of antibiotics and/or antiseptics into the coated implants to reduce the risk of infection in immunocompromised individuals or to be utilized in cases where people had infection and where their implants were being "swapped out" to permit the treatment of the infection while maintaining the structural integrity and rigidity of the surgery.

In one preferred embodiment, the implants are coated with a biodegradable Poly-L-Lactide (PLLA). Specifically, titanium plates and implants can be coated with this biodegradable semi-amorphous PLLA coating to the thickness of 30 microns thick. This PLLA coating is the carrier substance into which the antibacterial materials, which are preferably Rifampin and Fucidin, are integrated. The antiseptic materials used are preferably Octenidine and Irgasan. In this embodiment, as the Poly-L-Lactide degrades the antiseptic material and/or the antibiotic is released into the microenvironment surrounding the implant.

This allows sterilization of the area adjacent to the implant, and it prevents and/or inhibits the bacteria or infected agents entering the interstices of the metal implant. It also allows for the stabilization of the orthopaedic patient, and allows infections to be combated with antiseptic solutions and/or antibiotics. The use of antiseptics nowadays is possibly the way of the future as microbes, bacteria, and other infectious agents are becoming increasingly resistant to antibiotics. Clinical testing on New Zealand rabbits after titanium plate osteosynthesis shows considerable antibacterial activity around these coated implants. The implants have been quantitatively evaluated for bacterial growth and dosages have been determined to be effective in suppressing and eradicating infection adjacent to these implants. (See, e.g., J. of Orthopaedic Research 24, 2006.)

Accordingly, it seems clear that using an antibacterial biodegradable PLLA coating on titanium rods and plates would significantly reduce the infection rate in vitro and in vivo Antiseptic coatings would also lead to the reduction of infection rate. In addition, using antiseptics the possibility of antibiotic induced bacterial resistance would be obviated.

CONCLUSION

Unless otherwise specified, all of the references disclosed herein are incorporated by reference in to the specification.

Those skilled in the art will appreciate that the foregoing examples and descriptions of various preferred embodiments of the present invention are merely illustrative of the invention as a whole, and that variations in the coating methodologies of the present invention, may be made within the spirit and scope of the invention. Accordingly, the present invention is not Limited to the specific embodiments described herein but, rather, is defined by the scope of the appended claims.

What is claimed is:

1. An implant screw for permanent use in a patient comprising:
    an elongated shafted having a threaded portion for engaging a bone of the patient disposed along a distal portion thereof, an exposed head portion disposed at a proximal end thereof, and a fixture engaging portion disposed between said threaded portion and said exposed head portion;
    a porous and non-dissolvable biomimetic coating disposed on at least the portion of the thread configured to engage a bone, the biomimetic coating forming a non-dissolving interfacial binding region between the implant screw and the bone, said interfacial binding region comprising at least the biomimetic coating and bone;
    a dielectric coating disposed on at least the exposed head portion and the fixture engaging portion of the implant screw, the dielectric coating insulating the implant from secondary corrosive currents; and
    an infection preventative material, selected from one or all of an antimicrobial, an antibacterial or an antiseptic material, such infection preventative material being incorporated into at least the biomimetic coating, said infection preventative material continuously releasing a dose of an infection preventative material above a minimum inhibitory concentration into a region immediately adjacent said implant.

2. The implant screw of claim 1, wherein the infection preventative material is incorporated into both the biomimetic and dielectric coatings.

3. The implant screw of claim 1, wherein the infection preventative material is incorporated into a biodegradable polymer.

4. The implant screw of claim 3, wherein the biodegradable polymer is selected from the group consisting of PLA, PLLA, PDLLA, PGA, phosphate PLA, and PLGA.

5. The implant screw of claim 1, wherein the infection preventative material is selected from the group consisting of acidic antibiotics, and fibrinolytic agents.

6. The implant screw of claim 5, wherein the infection preventative material is an acidic antibiotic selected from the group consisting of fucidin, rifampin, amoxicillin, cephamandol, gentamicin, tobramycin, carbenicillin, cephalothin, and vancomycin.

7. The implant screw of claim 5, wherein the infection preventative material further comprises an ionic silver material selected from the group consisting of metallic silver, silver chlorides, silver oxides or silver nitrates.

8. The implant screw of claim 7, wherein the ionic silver material has a concentration of at least 10,000 parts per million.

9. The implant screw of claim 5, wherein the infection preventative material is a fibrinolytic agent selected from the group consisting of heparin, urokinase-heparin and fibronectin.

10. The implant screw of claim 1, wherein the infection preventative material is a carboxy containing antibiotic.

11. The implant screw of claim 1, wherein the infection preventative material is an antiseptic selected from one of either octenidine or irgasan.

12. The implant screw of claim 1, wherein the biomimetic coating comprises at least a material that is one of either an osteoconductive or osteoinductive substance.

13. The implant screw of claim 12, wherein the biomimetic coating is selected from the group consisting of ceramics, glass ceramics, apatites, plastics, plasmified titaniums, titanium oxides, fluorine, metals, porous metals, metal oxides, metal halides, carbonitrides and calcium phosphates.

14. The implant screw of claim 13, wherein the biomimetic coating is a calcium phosphate material selected from the group consisting of dicalcium phosphates, dihydrates, dihydrides, octacalcium phosphates, beta-tricalcium phosphates, hydroxyapatites, tetracalcium phosphates and monoxides.

15. The implant screw of claim 14, wherein the biomimetic coating is a hydroxyapatite with calcium/phosphorus ratio of about 1.67.

16. The implant screw of claim 12, wherein the biomimetic coating is an apatite material selected from the group consisting of fluoroapatite, crystalline oxyapatite, beta-wollastonite and beta-whitlockite.

17. The implant screw of claim 1, wherein the dielectric material coating disposed thereon is selected from the group consisting of titanium oxide and Parylene.

18. The implant screw of claim 1, wherein at least a portion of an outer surface of the implant screw is treated in accordance with a method selected from the group consisting of laser radiating, electron radiation, shot peening, micro texturing, ion implantation, roughening, degreasing and deburring.

19. The implant screw of claim 1, wherein at least a portion of at least the exposed head is configured to engage a separate metal component, and wherein the portion of the exposed head configured to engage a separate metal component has a dielectric coating disposed thereon.

* * * * *